United States Patent [19]

Ikenaka et al.

[11] Patent Number: 5,350,678
[45] Date of Patent: Sep. 27, 1994

[54] METHOD OF DIFFERENTIAL ASSAY FOR α-AMYLASE ISOZYMES AND A KIT FOR THE SAME

[75] Inventors: Tokuji Ikenaka, Sakai; Kaoru Omichi, Toyonaka, both of Japan

[73] Assignee: Wako Pure Chemical Industries, Ltd., Osaka, Japan

[21] Appl. No.: 884,252

[22] Filed: May 8, 1992

Related U.S. Application Data

[63] Continuation of Ser. No. 79,744, Jul. 30, 1987, abandoned.

[30] Foreign Application Priority Data

Aug. 1, 1986 [JP] Japan ................................. 61-181564

[51] Int. Cl.$^5$ ............................................. C12Q 1/40
[52] U.S. Cl. ......................................... 435/22; 435/18; 435/810
[58] Field of Search ........................... 435/22, 18, 810

[56] References Cited

FOREIGN PATENT DOCUMENTS 0104047 3/1984 European Pat. Off. .
0171960 2/1986 European Pat. Off. .
0201333 11/1986 European Pat. Off. .

OTHER PUBLICATIONS

Omichi et al. *Kagaku* (Kyoto) 1986, 41 (2), pp. 138–139 "Fluorogenic Substrates of Human α-Amylase. Discrimination Between Pancreatic and Salivary α Amylases".
Clin. Chim. Acta, 54, (1974) pp. 137–144.
Clin. Chem. 18, No. 12 (1972) pp. 1493–1496.
J. Biochemistry, 97, (1985) pp. 1357–1362.
Clin. Chem., 23 560 (1977).
Chemical Abstracts, vol. 106, No. 11, Mar. 16, 1987, p. 252, Col. 1.
Chemical Abstracts, vol. 101, No. 11, Oct. 10, 1984, p. 252, Col. 1.
Patent Abstracts of Japan, vol. 9, No. 331 (C–321 [2054], Dec. 25, 1985.
Clinical Chemistry, vol. 28, No. 7, Jul. 1982, pp. 1525–1527.

*Primary Examiner*—Christine M. Nucker
*Assistant Examiner*—Laurie Scheiner
*Attorney, Agent, or Firm*—Armstrong, Westerman, Hattori, McLeland & Naughton

[57] ABSTRACT

Differential assay of human pancreatic α-amylase and human salivary α-amylase can be made extremely easily with good accuracy using a reducing-end modified maltooligosaccharide derivative as a substrate, by acting coupled enzymes having different substrate specificities on the degradation products formed by the hydrolytic action of α-amylases and measuring the resulting reaction products.

14 Claims, 4 Drawing Sheets

METHOD OF DIFFERENTIAL ASSAY FOR α-AMYLASE ISOZYMES AND A KIT FOR THE SAME

This application is a continuation of application Ser. No. 079,744 filed Jul. 30, 1987, abandoned.

BACKGROUND OF THE INVENTION

1. Field of the Invention

The present invention relates to a novel method of differential assay for α-amylase isozymes and a kit for the same. More particularly, the present invention relates to a novel method of differential assay for human pancreatic α-amylase and human salivary α-amylase and a kit used for such a method. According to the method for measurement and the kit of the present invention, marked effects are achieved that differential assay for human pancreatic α-amylase and human salivary α-amylase can be extremely easily performed with good accuracy using a spectrophotometer, a fluorophotometer, etc. widely applied to the field of clinical examination and the method is readily applicable to an automated analyzer. The measurement method and kit of the present invention are thus extremely useful for daily clinical tests such as analysis of hyperamylasemia research for disease, etc.

2. Description of the Related Art

It is important for medical diagnosis to measure α-amylase activity in a vital sample, in particular, in human saliva, pancreatic juice, blood or urine. For example, in pancreatic disease, pancreatic cancer and parotitis, the α-amylase activity in blood or urine shows a marked rise as compared to the normal value.

In addition, for purposes of analyzing hyperamylasemia or research for disease, it is important to determine the α-amylase activity in blood, dividing into its isozyme, and such has been applied to daily clinical tests.

There are hitherto known various methods for separation of human pancreatic α-amylase and human salivary α-amylase, including (1) separation utilizing difference in charge [Clin. Chim. Acta, 54, 137, (1974)], (2) gel filtration [Clin. Chem., 18, 1493, (1972)], (3) a method utilizing affinity chromatography, (4) an immunological method [J. Biochemistry, 97, 1357, (1985)], (5) a method using an α-amylase inhibitor [Clin. Chem., 23, 560, (1977)], and the like.

Among them, methods that are currently applicable to clinical tests are (1) the method in which the separation is effected by electrophoresis utilizing difference in charge [Clinical Pathology, "An Analysis of Isoenzyme and its Significance", a Special Number 43, p. 17 (1981)] and (5) the method using an amylase inhibitor which has been frequently adopted recently.

Electrophoretic methods suited for clinical tests include a method using a cellulose acetate membrane or thin layer polyacrylamide gel, or the like but any of them involves defects that operations for the measurement are complicated and many hours is required for the measurement.

On the other hand, the method using the α-amylase inhibitor comprises, utilizing more potent inhibitory action of a wheat-derived amylase inhibitor on salivary α-amylase than on pancreatic α-amylase, determining the ratio of both amylases. At present, any inhibitor that specifically inhibits completely either pancreatic α-amylase or salivary α-amylase has not been found. In such a method, therefore, the ratio of pancreatic α-amylase activity to salivery α-amylase activity in a sample is read out from a calibration curve prepared using standard enzyme solutions of known concentrations. Such a method has been recently widely used because the measurement can be made relatively simply.

In order to determine the ratio of pancreatic α-amylase activity to salivary α-amylase activity according to this method, however, it is necessary to measure twice, i.e., in the case of using the inhibitor and in the case of using no inhibitor. Accordingly, the method still involves complicated operations.

On the other hand, the present inventors have already found out that the the the actions of the isozymes on oligosaccharide derivatives differs and that the ratio of products produced therefrom also differs depending upon the isozymes and filed a patent application directed to a method utilizing those findings for differential assay of α-amylase isozymes (European Patent Publication No. 104047). This method is concerned with differential assay of human pancreatic α-amylase and human salivary α-amylase which comprises using as a substrate oligosaccharide having a certain modifying group, namely, a modifying group having a fluorescent property or a modifying group which absorbs UV, and measuring degradation products formed upon hydrolysis with an α-amylase by high performance liquid chromatography. According to this method, the differential assay of α-amylase isozymes has become much easier than in the prior arts. In this method, however, special equipments such as high performance liquid chromatography, etc. must be used; in addition, the method has some problem such as time-consuming, and is not sufficiently satisfactory yet. It has thus been desired to develop a method for differential assay of α-amylase isozymes applicable to spectrophotometry, fluorophotometry, automated analyzers, etc. widely spread in the field of clinical tests and having excellent handling ability of samples.

SUMMARY OF THE INVENTION

An object of the present invention is to provide a method for differential assay of α-amylase isozyme in which pancreatic α-amylase and salivary α-amylase can be differentially assayed extremely easily using equipments such as a spectrophotometer, a fluorometer, an automatic analyzer, etc. widely spread in the field of clinical tests.

Another object of the present invention is to provide a kit for use in such a method for assay of α-amylase isozyme activity.

Further objects and advantages of the present invention will be apparent from the following description.

The present invention provides a method for differential assay of α-amylase isozymes which comprises reacting α-amylases in a sample with a reducing-end modified maltooligosaccharide derivative as a substrate, acting two kinds of coupled enzymes having different substrate specificities from each other on degradation products formed by the hydrolytic action of the α-amylases and measuring the resulting reaction products to assay human pancreatic α-amylase and human salivary α-amylase differentially.

The present invention also provides a kit for use in the aforesaid differential assay of α-amylase isozymes comprising:

a first solution comprising a reducing-end modified maltooligosaccharide derivative as a substrate and a coupled enzyme that specifically acts on one of the degradation products produced from the derivative by the action of α-amylases in a sample; and, a second solution comprising a coupled enzyme that non-specifically acts on the degradation products produced from the derivative by the action of α-amylases in the sample.

Figure 1:
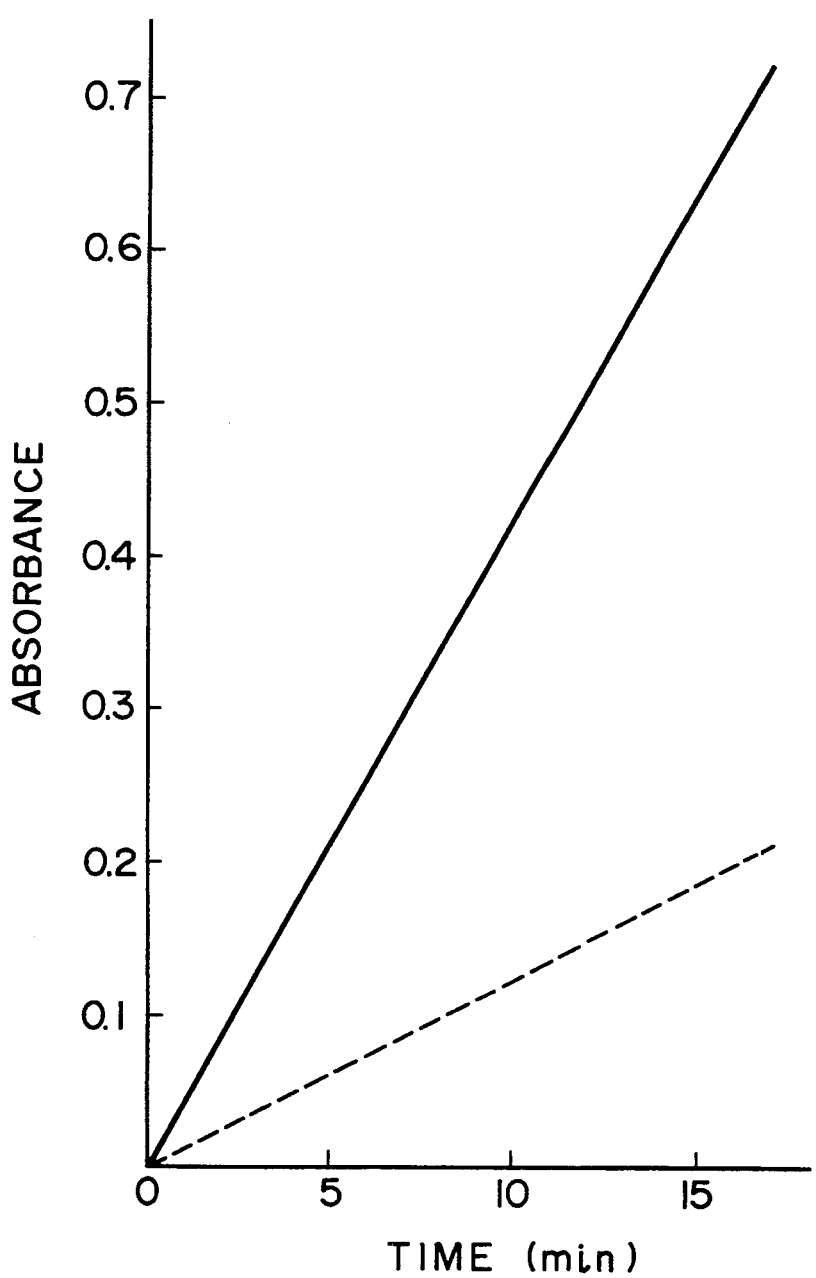
FIG. 1 shows the time courses of liberation of p-intro-phenol obtained in Example 1 by human pancreatic α-amylase in the first solution (dotted line) and in the second solution (solid line).

$$M = \frac{\Delta E_3/\text{min}}{(\Delta E_4/\text{min} \times 410/350)}$$

on the vertical axis, using the change in absorbance per min. in the first solution ($\Delta E_3$/min) and the change in absorbance per min. in the second solution ($\Delta E_4$/min), based on the ratio of human pancreatic α-amylase activity in the sample solution plotted on the abscissa.

DESCRIPTION OF THE PREFERRED EMBODIMENTS

The present invention is based on the finding that selectivity at the hydrolyzed sites when α-amylases composed of human pancreatic α-amylase and human salivary α-amylase hydrolyze the maltooligosaccharide derivatives modified at the reducing-end thereof, i.e., the hydroxy group —OH at the 1-position of the reducing-end glucose residue being substituted with —OR$^1$ (wherein R$^1$ represents an organic residue); in other words, a ratio of the degradation products formed by the hydrolytic action of α-amylases, is decided depending upon kind of isozymes, namely, human pancreatic α-amylase and human salivary α-amylase. According to the present invention, the differential assay of α-amylase isozymes, i.e., human pancreatic α-amylase and human salivary α-amylase, can be performed by reacting the degradation products formed upon hydrolysis of the maltooligosaccharide derivative in which the hydroxy group at the 1-position of the reducing-end glucose residue is substituted with —OR$^1$ by α-amylase isozymes in a sample with a coupled enzyme specifically acting on one of the degradation products such as modified glucose, reducing-end modified maltose derivative, reducing-end modified maltotriose derivatives, reducing-end modified maltotetraose derivatives, etc. and, with a coupled enzyme non-specifically acting on all of the degradation products such as modified glucose, reducing-end modified maltose derivative, reducing-end modified maltotriose, reducing-end modified maltotetrose derivatives etc., in sequence or independently, thereby to produce compounds of R$^1$—OH and measuring the produced compounds.

The measurement of the R$^1$—OH compound is performed by determining the absorbance, fluorescent intensity, etc. of the compound as will be later described.

In the present invention, the differential assay of α-amylase isozymes comprises determining, through the measurement of compound R$^1$—OH quantity A of a specific product formed by the hydrolytic action of α-amylase in a sample per a unit time period and quantity B of the whole substrates (namely, the total quantities of modified glucose; and the reducing-end modified degradation products such as reducing-end modified maltose derivative, reducing-end modified maltotriose derivative, reducing-end modified maltotetraose derivative, etc.) formed by the hydrolytic action of α-amylases in the sample per a unit time period, calculating its ratio A/B and utilizing the ratio being in a linear relation to the ratio of the two α-amylase isozymes co-present.

The reducing-end modified maltooligosaccharide derivatives which can be used in the present invention .are preferably straight chain oligosaccharide derivatives having from 4 to 7, more preferably 5 or 6 glucose residues, in which the hydroxy group —OH at the 1-position of the reducing-end glucose residue is substituted with —OR$^1$ (wherein R$^1$ represents an organic residue). Representative examples of R$^1$ for the substituent —OR$^1$ are organic residues etc., represented by formulae (I), (II) and (III) described below;

(I)

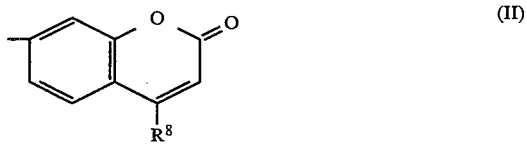

(II)

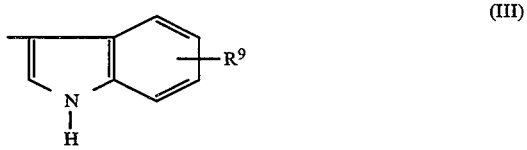

(III)

In formula (I), R$^3$ to R$^6$ independently represent hydrogen, a lower alkyl group, a lower alkoxy group, nitro group, a carboxyl group, a sulfonic acid group or a halogen, etc.,; R$^3$ and R$^5$, and/or R$^4$ and R$^6$, may be bonded to form an aromatic ring; and R$^7$ represents hydrogen, a lower alkoxy group, a halogen or a nitro group. In formula (II), R$^8$ represents hydrogen, methyl group or trifluoromethyl group. In formula (III ), R$^9$ represents hydrogen or a halogen.

As the phenoxy group which may optionally have a substituent(s) thereon or the naphthoxy group which may optionally have a substituent(s) thereon, which is usable as —OR$^1$ wherein R$^1$ is represented by formula (I), any groups are usable as far as they are groups capable of binding to the reducing-end glucose residue of the oligosaccharide and being hydrolyzed by the action of glucoamylase [E.C.3.2.1.3.], α-glucosidase [E.C.3.2.1.20.], β-glucosidase [E.C.3.2.1.21.], isomaltase [E.C.3.2.1.10] or β-amylase [E.C.3.2.1.2.], etc. and further capable of producing $R^1$—OH upon the hydrolysis, which have absorption in a visible region like nitrophenols, or groups capable of forming dyes upon coupling with couplers by the action of oxidases such as catechol oxidase, laccase, tyrosinase or monophenol oxidase, etc., or those capable of producing dyes upon coupling with couplers by the action of oxidizing agents. Specific examples of $R^1$ in formula (I) that satisfies the foregoing requirements include p-nitrophenyl group, m-nitrophenyl group, o-chlorophenyl group, p-chlorophenyl group, 2,6-dichlorophenyl group, o-methoxyphenyl group, p-methoxyphenyl group, o-methylphenyl group, o-carboxyphenyl group, o-sulfophenyl group, 1-naphthyl group, 2-sulfo-1-naphthyl group, 2-carboxy-1-naphthyl group, etc. but $R^1$ is not limited thereto.

Concrete examples of the umbelliferyl group that may optionally have a substituent thereon, which is usable as —$OR^1$ wherein $R^1$ is represented by formula (II), include umbelliferyl group wherein $R^8$ is hydrogen, 4-methylumbelliferyl group wherein $R^8$ is methyl group, 4-trifluoromethylumbelliferyl group wherein $R^8$ is trifluoromethyl group, etc.

Concrete examples of the indoxyl group that may optionally have a substituent thereon, which is usable as $OR^1$ wherein $R^1$ is represented by formula (III), include indoxyl group, 5-bromoindoxyl group, 4-chloro-3-bromoindoxyl group, etc.

The site to be modified by the reducing-end modifying group is generally at the 1-position of the reducing-end glucose residue but is not particularly limited thereto. For example, a reducing-end modified maltooligisaccharide having a structure in which phosphoric acid is bound to the hydroxy group at the 6-position thereof can also be satisfactorily employed as the substrate in the present invention.

The non-reducing-end glucose residue of the maltooligosaccharide derivative in accordance with the present invention may be or may not be modified. In general, examples of the modifying group for the non-reducing-end glucose residue includes substituents having a fluorescent property such as 2-pyridylamino group, 3-pyridylamino group, etc.; substituents having UV absorption such as anilino group, methylanilino group, hydroxyanilino group, carboxyphenylamino group, etc.; substituted alkoxy groups such as methoxy group, ethoxy group, etc.; substituted alkoxy groups such as carboxymethoxy group, hydroxyethoxy group, etc.; halogen atoms such as chlorine, bromine, etc.; an amino group; etc. In addition to these groups, for example, glucuronic acid in which the —$CH_2OH$ group at the 6-position of the non-reducing-end glucose residue is substituted with —COOH group, a hydrazone derivative in which the —$CH_2OH$ group at the 6-position thereof likewise takes a hydrazone structure as in —CH=N—$NH_2$ or

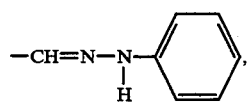

those forming a cyclic structure by the —OH group at the 4-position thereof and the —$CH_2OH$ group at the 6-position thereof such as 4,6-O-benzylidene, 4,6-O-methylene, 4,6-O-ethylidene, 4,6-O-isopropylidene, etc., can also be employed, as the modifying group of the non-reducing-end glucose residue in guide the same manner for the purpose of the present invention.

These reducing-end modified maltooligosaccharide in accordance with the present invention can be readily synthesized, with respect to those in which the non-reducing-end glucose residue is not modified, by the process desired in, for example, Carbohydrate Research, 60, 359–368 (1968), etc.; and, when the non-reducing-end glucose residue is modified, by the processes described in, for example, Published Unexamined Japanese Patent Application KOKAI No. 237998/85, European Patent Publication Nos. 135758 and 173255 etc.

As the coupled enzymes in accordance with the present invention, there are enzymes that act specifically on one of the degradation products and enzymes that act non-specifically on the degradation products. Examples of the enzymes that act specifically on modified glucose substituted with —$OR^1$ or on one of the degradation products such as reducing-end modified maltose derivative, reducing-end modified maltotriose derivatives, reducing-end modified maltotetraose derivatives, wherein the hydroxy group of the reducing-end glucose residue is substituted with —$OR^1$, include isomaltase (E.C.3.2.1.10.) which acts specifically on modified glucose wherein the modifying group at the 1-position thereof is α-linked, β-amylase (E.C.3.2.1.2.) which acts specifically on the reducing-end modified maltose derivative, β-glucosidase (E.C.3.2.1.21.) which acts specifically on modified glucose wherein the modifying group at the 1-position thereof is β-linked, etc. The specifically acting enzyme can be used in combination of two or more. The non-specifically acting enzymes are enzymes that non-specifically act on the degradation products described above and examples include glucoamylase (E.C.3.2.1.3.), α-glucosidase (E.C.3.2.1.20.), etc. The non-specifically acting enzyme may also be used in combination of two or more. These coupled enzymes are not limited thereto unless functions of enzymes are contrary to the gist of the present invention.

The compound $R^1$—OH which is formed by the action of the coupled enzymes is measured as follows.

Namely, in case that $R^1$—OH is a nitrophenol derivative such as p-nitrophenol, its absorbance (for example, absorbance at 400 nm) are measured; in case that $R^1$—OH is a phenol or naphthol derivative containing no nitro group therein (though the nitro group may be contained), for example, phenol, o-cholorophenol, 2,6-dichlorophenol, p-methoxyphenol, etc., oxidases such as catechol oxidase, laccase, tyrosinase or monophenol oxidase, etc. or oxidizing agents such as iodic acid, periodic acid, etc. or peroxidase and hydrogen peroxide are reacted with $R^1$—OH to couple (oxidatively condense) with couplers such as 4-aminoantipyrine, 3-methyl-2-benzothiazolinone hydrazone (MBTH), etc., whereby the absorbance of the resulting dye is measured. In case that $R^1$—OH is a compound emitting a fluorescence such as umbelliferone or 4-methylumbelliferone, its fluorescent intensity is measured. In case that $R^1$—OH is indoxyl, the absorbance of the indigo dye formed by oxidation is measured.

To practice the present invention, for example, there are prepared the first solution comprising the reducing-end modified maltooligosaccharide derivative as a substrate and the coupled enzyme which specifically acts on one of the degradation products produced from the derivative by the action of α-amylases in a sample; and, the second solution comprising the coupled enzyme which non-specifically acts on the degradation products produced from the derivative by the action of α-amylases in a sample. A sample is added to these solutions and, quantity A of the degradation product which reacts with the specifically acting coupled enzyme per a unit time period and quantity B of the whole degradation products produced by the action of α-amylases which react with the non-specifically acting coupled enzyme, i.e., quantity of the whole substrates degraded by the hydrolytic action of α-amylases per unit time period are determined by measuring the products formed by acting the coupled enzyme on the α-amylase hydrolysates.

In determining A and B, a sample is added to the first solution and the second solution, respectively, to determine A and B separately (in this case, the same substrate as used in the first solution should be, as a matter of course, added to the second solution); alternatively, a sample is added to the first solution to determine A and the second solution is then added to the system to determine B (in this case, however, it is preferred to correct amounts of the solutions.). Any procedure may be used for the determination of A and B.

From the determined A and B, a ratio of A/B is calculated. Based on a calibration curve between a ratio of A/B previously prepared using a standard sample having a known concentration of both α-amylases, the ratio of isozymes, for example, human pancreatic α-amylase activity and human salivary α-amylase activity in the sample is determined; using this value and the value of the total activity of α-amylases determined from B, the each activity value of human pancreatic and human salivary α-amylase can be determined.

In the present invention, the concentration of the reducing-end modified maltooligosaccharide derivative used as a substrate is not particularly restricted but is, in general, preferably about 0.1 to 10 mM.

Samples to be measured in the present invention can be any one as far as they contain α-amylases composed of human pancreatic α-amylase and human salivary α-amylase and, mention may be made of body fluids such as blood, serum, urine, etc. Sources and origins of glucoamylase, α-glucosidase, β-glucosidase, isomaltase, β-amylase, etc. which are the coupled enzymes are not particularly limited but any enzyme derived from animals, plants and microorganisms is usable. The amount of these coupled enzymes is generally 0.1 to 100 units/ml, preferably 0.5 to 70 units/ml in the reagent mixture.

Conditions for the measurement upon the practice of the present invention are not particularly limited but are preferably at temperatures of approximately 25° to 40° C. and a reaction time period can be freely chosen depending upon purpose.

The optimum pH is not particularly limited but a preferred pH is in a range of approximately 6 to 8. Buffers for maintaining the optimum pH can freely be chosen; for example, there can be freely chosen phosphates, tris(hydroxymethyl)aminomethane-hydrochloride, Good's buffer or the like.

Further as an activator of the α-amylase, there can be used, for example, sodium chloride, calcium chloride, potassium chloride, etc.

Examples of the couplers used for coupling (oxidative condensation) with the phenols or naphthols released by the action of the coupled enzymes include 4-aminoantipyrine, 3-methyl-2-benzothiazolinone hydrazone (MBTH), p-amino-N,N-diethylaniline, etc. but the couplers are not limited thereto. As the oxidases for coupling (oxidative condensation) of the phenols or naphthols with the couplers, there can be used laccase, catechol oxidase, tyrosinase, monophenol oxidase, etc.; any oxidase derived from animals, plants and microorganisms can be utilized generally in a range of 0.2 to 10 units/ml, preferably 0.5 to 4 units/ml. As the oxidizing agent for the coupling (oxidative condensation), there are iodic acid or/and salts thereof, periodic acid or/and salts thereof, hydrogen peroxide, etc. but the agent is not limited thereto.

Further in the method for the measurement of the present invention, the differential assay is performed by rate assay which comprises measuring absorbance of the released nitrophenol derivative or indigo dye; oxidatively coupling the released phenol or naphthol derivative with 4-aminoantipyrine, MBTH, etc. and measuring the changes of the absorbance of the resulting dye; or measuring the changes of fluorescent intensity of the released umbelliferone derivative and therefore, the measurement system of the present invention is not affected by sugars such as glucose, maltose, etc., reductive substances such as ascorbic acid, etc. or bilirubin or the like that are present in a sample.

Furthermore the measurement method of the present invention is well suited for any automated analysis device and can be performed by any of manual and automated analyses, depending upon necessity.

As is apparent from the foregoing description, the kit used for the differential assay of α-amylase isozymes according to the present invention comprises:

the first solution comprising the reducing end-modified maltooligosaccharide derivative as a substrate and the coupled enzyme that specifically acts on one of the degradation products produced from the derivative by the action of the α-amylases in a sample; and, the second solution comprising the coupled enzyme that non-specifically acts on the degradation products produced from the derivative by the action of the α-amylases in the sample.

The second solution may contain the reducing-end modified maltooligosaccharide derivative in case that the sample is added to the first solution and second solution, respectively, to determine A and B separately.

In addition to these first and second solutions, color forming system reagents for measurement of the products formed by the action of the coupled enzymes are supplemented as a part of the kit. Examples of these reagents include, in the case of measuring nitro-free phenol or naphthol derivative released by the action of the coupled enzymes, oxidases such as catechol oxidase, laccase, tyrosinase or monophenol oxidase; oxidizing agents such as iodic acid or periodic acid; couplers such as 4-aminoantipyrine, 3-methyl-2-benzothiazolinone hydrazone (MBTH), etc.

Further the kit may additionally include buffers for maintaining the optimum pH which are required to conduct the assay of the present invention at the optimum pH, for example, phosphates, tris(hydroxymethyl)aminomethane-hydrochloride, Good's buffer, etc.

In addition, other reagents and addenda may also be added to the kit of the present invention in such a manner that does not adversely affect the fundamental nature of the differential assay of the present invention.

As has been described above, the present invention is to provide the differential assay method of novel α-amylase isozymes and the kit used for the method. According to the method of the present invention, the assay can be performed extremely easily with good accuracy using a spectrophotometer or a fluorophotometer widely used in the field of clinical tests and can be readily applied to automated analyzers, etc. and therefore, the present invention achieves marked effects and greatly contributes to the art.

The present invention will be described in more detail with reference to the examples below but is not deemed to be limited thereto.

EXAMPLE 1

Differential assay using p-nitrophenyl O-6-deoxy-6-[(2-pyridyl) amino]-α-D-glucopyranosyl-(1→4)-O-α-D-glucopyranosyl-(1→4)-O-α-D-glucopyranosyl-(1→4)-O-α-D-glucopyranosyl-(1→4)-α-D-glucopyranoside (hereafter simply referred to as FG5P)

Preparation of sample (1) First solution

A first solution was prepared by dissolving 26 mg of FG5P and 25 units of isomaltase in 50 ml of 0.08 M 3,3-dimethylglutarate-NaOH buffer (pH 6.9, containing 20 mmol/l of NaCl).

(2) Second solution

A second solution was prepared by dissolving 26 mg of PG5P and 1150 units of α-glucosidase in 50 ml of 0.08 M 3,3-dimethylglutarate-NaOH buffer (pH 6.9, containing 20 mmol/l of NaCl).

(3) Enzyme sample solutions

Human salivary α-amylase (manufactured by Sigma Co., Ltd.) and human pancreatic α-amylase prepared from human pancreatic juice were adjusted to 5.5 units/l, respectively and then these amylases were mixed in ratios of 3:1, 1:1 and 1:3.

Method

To 300 μl of the first solution or second solution preliminarily heated to 30° C. was added 50 μl of the enzyme sample solution. After thoroughly mixing them, the mixture was kept at 30° C. Change in absorbance of the reaction mixture with time was measured at 400 nm using as a blank the mixture obtained by adding 50 μl of purified water to the first solution and thoroughly mixing them in the case of using the first solution, and the mixture obtained by adding 50 μl of purified water to the second solution and thoroughly mixing them in the case of using the second solution.

Results

Figure 2:
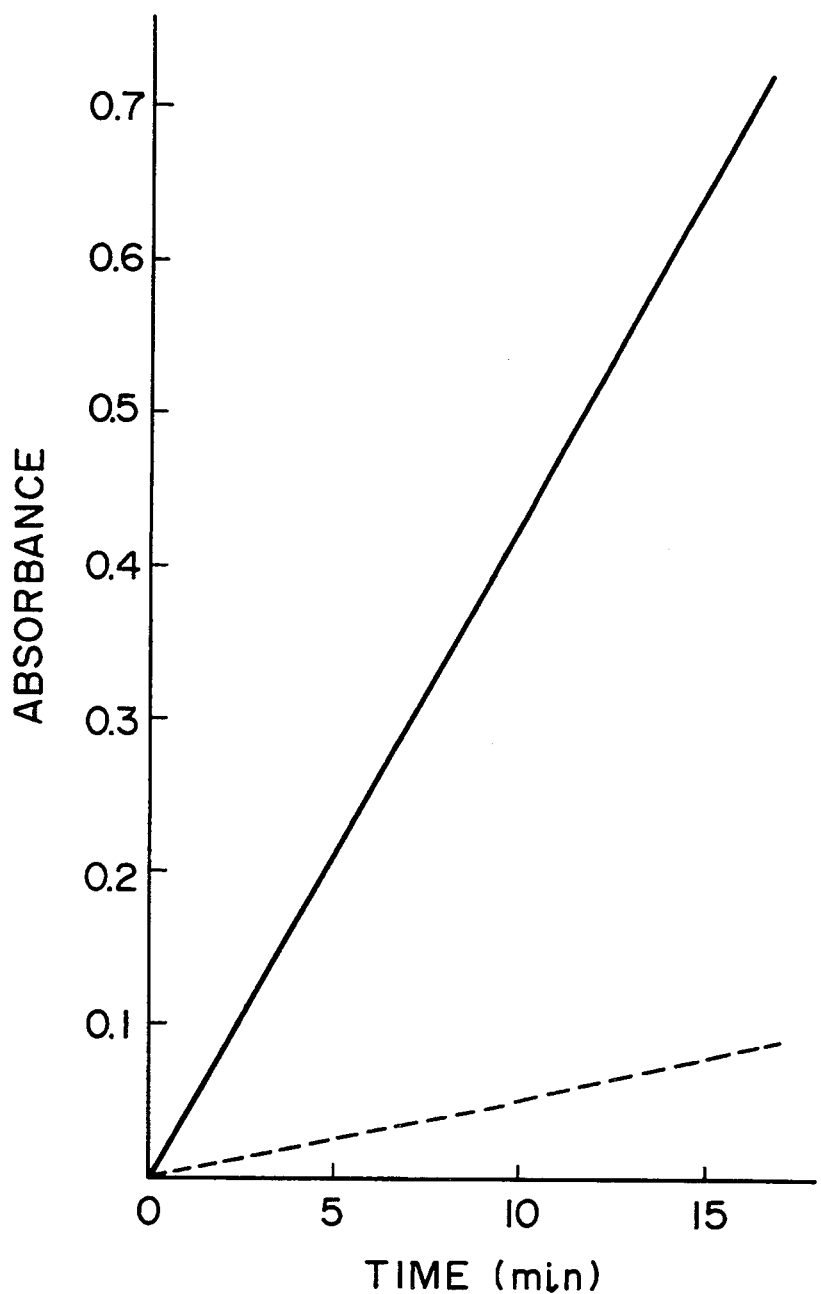
FIG. 2 shows the time courses of liberation of p-nitrophenol obtained in Example 1 by human salivary α-amylose in the first solution (dotted line) and in the second solution (solid line).

The changes in absorbance with time are shown in FIG. 1 and FIG. 2. FIGS. 1 and 2 indicate the results obtained using as the sample the enzyme sample solutions containing human pancreatic α-amylase and human salivary α-amylase, respectively. In the figures, the dotted line (....) and the solid line (—) indicate the results with the first solution and with the second solution, respectively.

As is clear from FIGS. 1 and 2, the changes in absorbance with the passage of time obtained by the reaction with the first solution are different between human pancreatic α-amylase and human salivary α-amylase; whereas in the reaction with the second solution, no difference is noted therebetween.

Further each enzyme sample solution was reacted with the first solution or the second solution and, the change in absorbance per min. in the first solution ($\Delta E_1$/min) and the change in absorbance per min. in the second solution ($\Delta E_2$/min) were determined. The relationship between $\Delta E_1$/min/$\Delta E_2$/min and the ratio of human pancreatic α-amylase activity in the sample solution is shown in FIG. 3.

Figure 3:
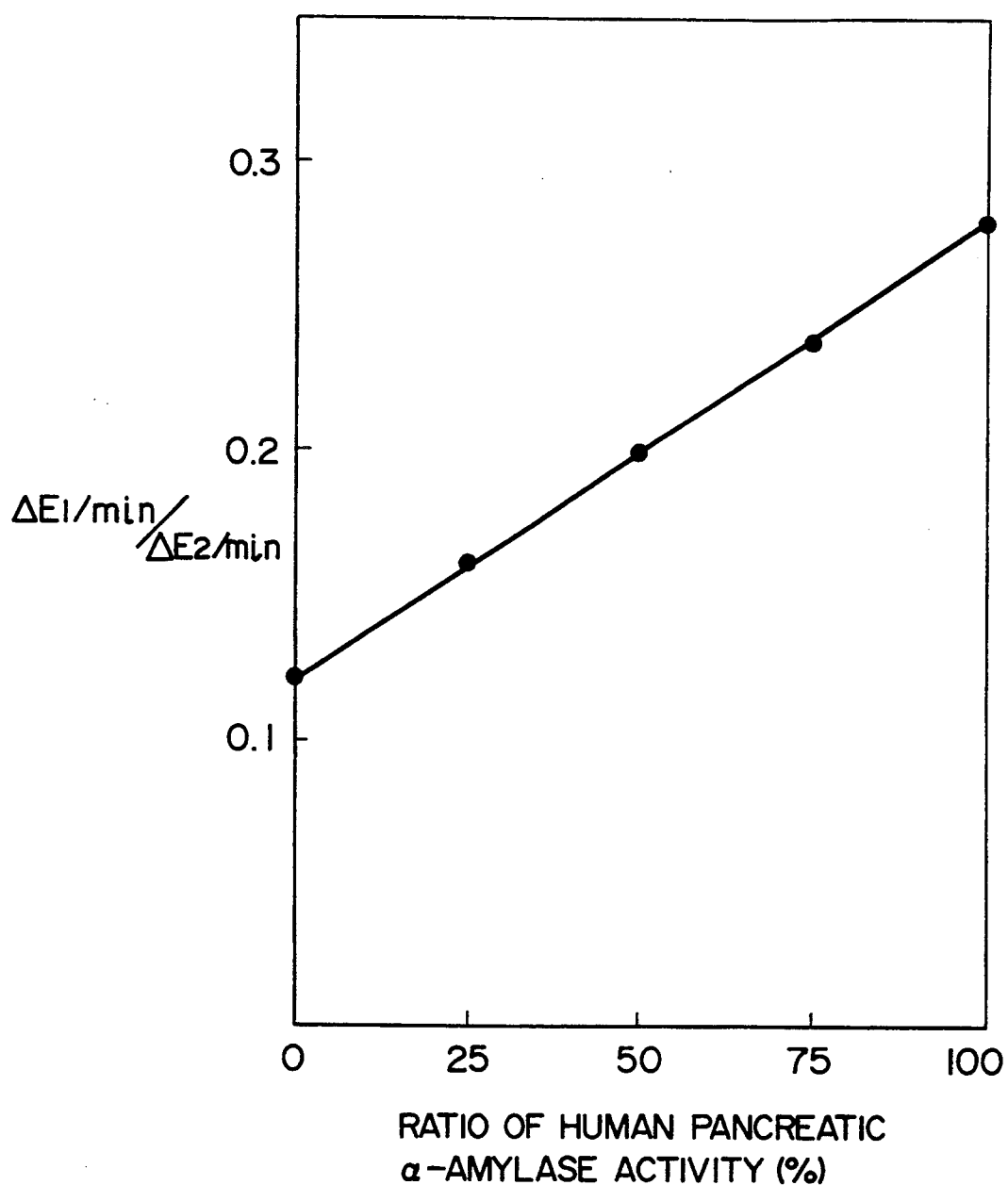
FIG. 3 shows the standard curve obtained in Example 1 between the ratio of human pancreatic α-amylase activity in the sample solution and the change in absorbance per minute in the first solution ($\Delta E_1$/min) to the change in absorbance per minute in the second solution. ($\Delta E_2$/min):
$\Delta E_1/\text{min}/\Delta E_2/\text{min}$

As is clearly noted from FIG. 3, a good linear relationship was obtained between $\Delta E_1$/min/$\Delta E_2$/min and the ratio of human pancreatic α-amylase activity.

EXAMPLE 2

Differential assay using p-nitrophenyl O-(2-O-carboxymethyl)-α-D-glucopyranosyl-(1→4)-O-α-D-glucopyranosyl-(1→4)-O-α-D-glucopyranosyl-(1→4)-O-α-D-glucopyranosyl-(1→4)-α-D-glucopyranoside (hereinafter simply referred to as 2CMG5P)

Preparation of sample (1) First solution

A first solution was prepared by dissolving 150 mg of 2CMG5P and 30 units of isomaltase in 50 ml of 0.05 M [2-(N-morpholino)ethanesulfonate] (hereafter simply referred to as MES)-NaOH buffer (pH 6.9, containing 1 mmol/l of CaCl$_2$).

(2) Second solution

A second solution was prepared by dissolving 2500 units of α-glucosidase and 1250 units of glucoamylase in 50 ml of 0.05 M MES-NaOH buffer (pH 6.9, containing 1 mmol/l of CaCl$_2$).

(3) Enzyme sample solutions

Enzyme sample solutions were prepared as in Example 1.

Method

To 300 μl of the first solution preliminarily incubated to 30° C. was added 50 μl of the enzyme sample solution. After thoroughly mixing them, the mixture was kept at 30° C. The change ($\Delta E_3$/min) in absorbance per min. of the reaction mixture was measured at 400 nm. Further 60 μl of the second solution preliminarily incubated to 30° C. was added to the reaction mixture followed by thorough mixing. While maintaining the reaction mixture at 30° C., the change ($\Delta E_4$/min) in absorbance per min. was measured 2 min. after the addition of the second solution.

A variable M was calculated according to the following equation:

$$M = \frac{\Delta E_3/\text{min}}{(\Delta E_4/\text{min} \times 410/350)}$$

Results

Figure 4:
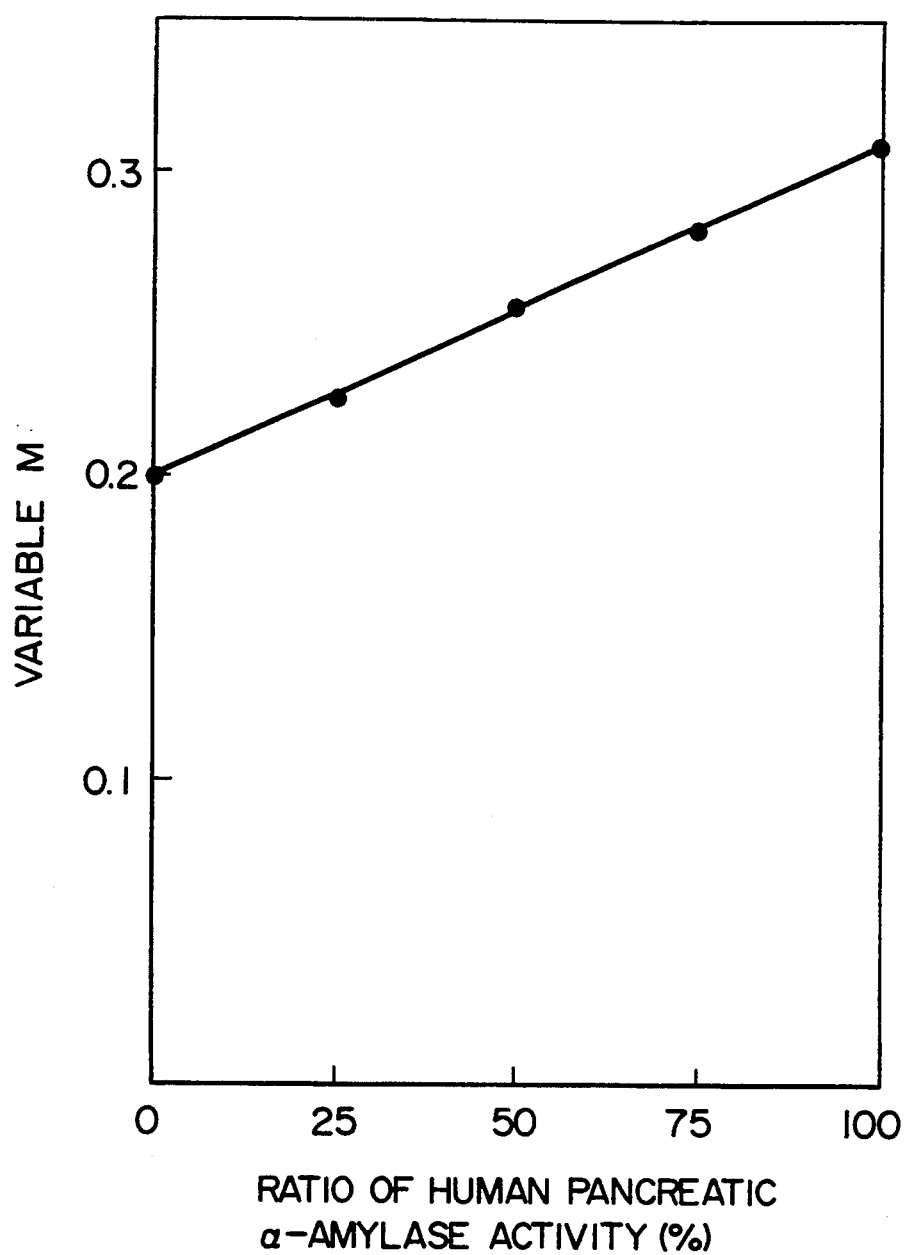
FIG. 4 shows a calibration curve obtained in Example 2, which is obtained by connecting points plotted variable M calculated according to the following equation.

The relationship between the ratio of human pancreatic α-amylase activity and the variable M is shown in FIG. 4.

As is evident from FIG. 4, a good linear relationship was obtained between the ratio of human pancreatic α-amylase activity and the valiable M.

What is claimed is:

1. A method for the differential assay of human pancreatic α-amylase and human salivary α-amylase isozymes in a sample containing at least one of said isozymes comprising:

a) i) preparing a maltooligosaccharide derivative in which the hydroxy group at the 1-position of the reducing-end glucose residue is substituted with —OR$^1$, wherein R$^1$ represents an organic residue, selected from the group consisting of compounds represented by formulae (I), (II), and (III),

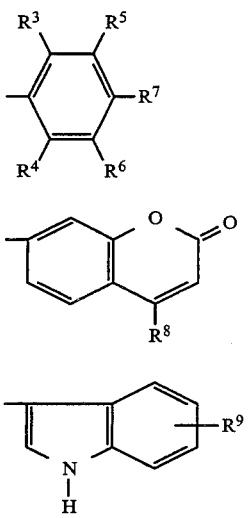

wherein $R^3$ to $R^6$ may be the same or different and are selected from the group consisting of hydrogen, a lower alkoxy group, a nitro group, a carboxyl group, a sulfonic acid group or an halogen, and $R^3$ together with $R^5$, and $R^4$ together with $R^6$, may be bonded to each other to form an aromatic ring, and $R^7$ represents hydrogen, a lower alkoxy group, an halogen or a nitro group, $R^8$ represents hydrogen, a methyl group or a trifluoromethyl group, and $R^9$ represents hydrogen or an halogen; and (ii) preparing a solution of said maltooligosaccharide derivative and a first enzyme selected from the group consisting of isomaltase, β-glucosidase and β-amylase; wherein the first enzyme specifically acts on one of reducing-end modified degradation products produced from said derivative by the hydrolytic action of α-amylase(s) in said sample and in which the hydroxy group at the 1-position of the reducing-end glucose residue thereof is substituted with said —$OR^1$ to release a compound $R^1OH$;

(iii) adding to said solution said sample containing α-amylase isozymes; and (iv) measuring a quantity A by an optical method, the quantity A being the rate of increase in optical change corresponding to the appearance of $R^1OH$ as a result of the action of said first enzyme on one of the reducing-end modified degredation products produced by the action of α-amylase on said maltooligosaccharide (v) adding at least one second enzyme that nonspecifically acts on said reducing-end modified degredation products to release the compound $R^1OH$;

(vi) measuring a quantity B by an optical method, the quantity B being the rate of increase in optical change corresponding to the appearance of $R^1OH$ as a result of the action of said second enzyme on the reducing-end modified degredation products produced by the action of α-amylase(s) on said maltooligosaccharide derivative; and c) determining the ratio of human pancreatic α-amylases and human salivary α-amylase in said sample from the ratio A/B using a standard curve.

2. A method for differential assay according to claim 1, wherein said maltooligosaccharide derivative is a straight chain oligosaccharide derivative having from 4 to 7 glucose residues.

3. A method for differential assay according to claim 1, wherein $R^1$ is an organic residue represented by formula (I), (II) or (III) below:

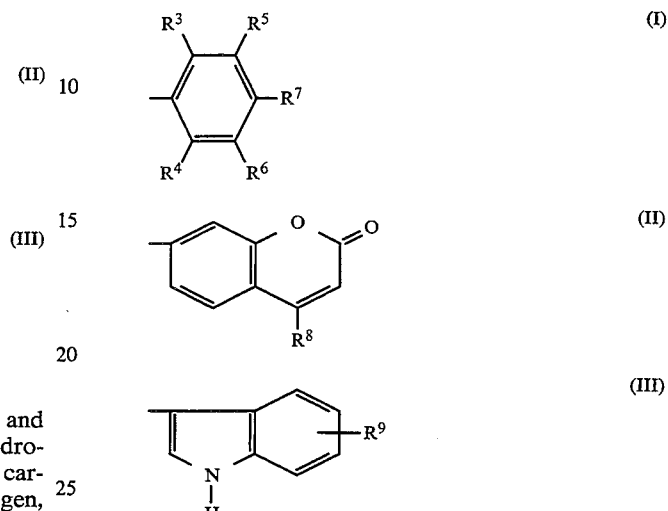

wherein, in formula (I), $R^3$ to $R^6$ independently represent hydrogen, a lower alkyl group, a lower alkoxy group, a nitro group, a carboxyl group, a sulfonic acid group or a halogen; $R^3$ and $R^5$, and/or $R^4$ and $R^6$, may be bonded to form an aromatic ring; and $R^7$ represents hydrogen, a lower alkoxy group, a halogen or a nitro group; in formula (II), $R^8$ represents hydrogen, methyl group or trifluoromethyl group; in formula (III), $R^9$ represents hydrogen or a halogen.

4. A method for the differential assay of α-amylase isozymes according to claim 1, wherein said first enzyme is an enzyme which cleave specifically a modified glucose in said degradation products, wherein the hydroxy group at the 1-position of glucose is substituted with —$OR^1$, or on a modified maltooligosaccharide in said degradation products wherein the hydroxy group at the 1-position of a reducing-end glucose residue is substituted with —$OR^1$, and wherein $R^1$ represents an organic residue.

5. A method for the differential assay of α-amylase isozymes according to claim 4, wherein said first enzyme is an enzyme selected from the group consisting of a) isomaltase cleaving specifically modified glucose in which the hydroxy group at the 1-position of glucose is substituted with —$OR^1$, wherein $R^1$ is α-linked at the 1-position thereof, b) β-glucosidase cleaving specifically modified glucose in which the hydroxy group at the 1-position of glucose is substituted with —$OR^1$, wherein $R^1$ is β-linked at the 1-position thereof, and c) β-amylase cleaving specifically modified maltose in which the hydroxy group at the 1-position of reducing-end glucose residue is substituted with —$OR^1$, wherein $R^1$ is α-linked at the 1-position thereof, and wherein $R^1$ represents an organic residue.

6. A method for the differential assay of α-amylase isozymes according to claim 1, wherein said second enzyme is an enzyme which cleaves non-specifically modified glucose, modified maltose, modified maltotriose and modified maltotetraose residues in said degradation products, wherein the hydroxy group at the 1-position of glucose or reducing-end glucose residue is substituted with —$OR^1$, and wherein $R^1$ represents an organic residue.

7. A method for differential assay according to claim 6, wherein said second enzyme is at least one selected from the group consisting of glucoamylase and α-glucosidase.

8. A method for the differential assay of α-amylase isozymes according to claim 1, wherein said optical method is selected from the group consisting of absorbance and fluorescence intensity.

9. A method for the differential assay of human pancreatic α-amylase and human salivary α-amylase isozymes in a sample containing at least one of said isozymes comprising:

(i) preparing a first solution comprising a maltooligosaccharide derivative in which the hydroxy group at the 1-position of the reducing-end glucose residue is substituted with —$OR^1$, wherein $R^1$ represents an organic residue, selected from the group consisting of compounds represented by formulae (I), (II), and (III),

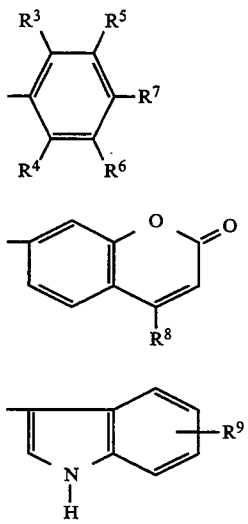

wherein $R^3$ to $R^6$ may be the same or different and are selected from the group consisting of hydrogen, a lower alkoxy group, a nitro group, a carboxyl group, a sulfonic acid group or a halogen, and $R^3$ together with $R^5$, and $R^4$ together with $R^6$, may be bonded to each other to form an aromatic ring, and $R^7$ represents hydrogen, a lower alkoxy group, an halogen or a nitro group, $R^8$ presents hydrogen, a methyl group or a trifluoromethyl group, and $R^9$ presents hydrogen, a methyl group or a trifluoromethyl group, and $R^9$ represents hydrogen or an halogen, and with a first enzyme from the group consisting of isomaltase, β-glucosidase and β-amylase that specifically acts on one of the degradation products produced from said derivative by the hydrolytic action of α-amylase(s) in said sample; β-glucosidase and a second solution comprising with or without said derivative at least one coupled enzyme that non-specifically acts on the degradation products produced from said maltooligosaccharide derivative by the action of α-amylase(s) in said sample;

(ii) contacting said sample with said first solution and then with said second solution without said derivative, or contracting said sample with said first solution and with said second solution with said derivative, respectively;

(iii) measuring by an optical method a quantity A of the reaction product per unit of the appearance of $R^1OH$ formed by the action of said first coupled enzyme in said first solution from the degradation products of α-amylase(s) in said sample; and measuring by an optical method a quality B of the reaction product per unit time formed by the action of said second coupled enzyme in said second solution from the degradation products of α-amylase(s) in said sample; and (iv) determining the ratio of human pancreatic α-amylase and human salivary α-amylase in the sample from the ratio A/B using a standard curve.

10. A method for differential assay according to claim 9, wherein said quantity A and quantity B are determined by separately adding the first solution and the second solution to the sample.

11. A method for differential assay according to claim 9, wherein the sample is added to the first solution to determine said quantity A and the second solution is then added the mixture to determine quantity B.

12. A method for differential assay according to claim 9, which is performed by directly measuring an absorbance of the reaction product formed by the action of said first enzyme in the first solution or the reaction product formed by the action of said second enzyme in the second solution, by measuring an absorbance of a dye produced from said reaction products or by measuring a fluorescent intensity of said reaction products.

13. A method for the differential assay of α-amylase isozymes according to claim 9, which comprises:
determining the ratio of human pancreatic α-amylase and human salivary α-amylase in the sample from the ratio A/B based on a calibration curve between the A/B value and the ratio of human pancreatic α-amylase activity and human salivary α-amylase activity prepare by using a standard sample having a known concentration of each of said α-amylases.

14. A method for the differential assay of α-amylase isozymes according to claim 9, wherein said first enzyme is an enzyme selected from the group consisting of
a) isomaltase cleaving specifically modified glucose in which the hydroxy group at the 1-position of glucose is substituted with —$OR^1$, wherein $R^1$ represents an organic residue and is α-linked at he 1-position thereof,
b) β-glucosidase cleaving specifically modified glucose in which the hydroxy group at the 1-position of glucose is substituted with —$OR^1$, wherein $R^1$ represents an organic residue and is β-linked at the 1-position thereof and
c) β-amylase cleaving specifically modified maltose in which the hydroxy group at the 1-position of reducing-end glucose residue is substituted with —$OR^1$, wherein $R^1$ represents an organic residue and is α-linked at the 1-position thereof;
and said second coupled enzyme is selected from the group consisting of glucoamylase and α-glucosidase.

* * * * *